(12) United States Patent
Lewis et al.

(10) Patent No.: US 7,482,601 B2
(45) Date of Patent: Jan. 27, 2009

(54) RADIATION SENSITIVE FILM INCLUDING A MEASURING SCALE

(75) Inventors: David F. Lewis, Monroe, CT (US); Carl A. Listl, New Hyde Park, NY (US); Xiang Yu, Bridgewater, NJ (US)

(73) Assignee: ISP Investments Inc., Wilmington, DE (US)

(*) Notice: Subject to any disclaimer, the term of this patent is extended or adjusted under 35 U.S.C. 154(b) by 243 days.

(21) Appl. No.: 11/282,095

(22) Filed: Nov. 17, 2005

(65) Prior Publication Data

US 2007/0019790 A1    Jan. 25, 2007

Related U.S. Application Data

(60) Provisional application No. 60/701,850, filed on Jul. 22, 2005.

(51) Int. Cl.
G01T 1/08 (2006.01)
G01D 18/00 (2006.01)

(52) U.S. Cl. .............. 250/474.1; 378/163; 378/164; 378/207; 250/472.1; 250/484.5

(58) Field of Classification Search ............. 378/163, 378/164, 206, 207; 250/472.1, 474.1, 484.5
See application file for complete search history.

(56) References Cited

U.S. PATENT DOCUMENTS

| | | | | |
|---|---|---|---|---|
| 2,399,424 A | * | 4/1946 | Bliss | 378/192 |
| 2,650,308 A | | 8/1953 | Catlin | |
| 4,734,355 A | * | 3/1988 | Lewis et al. | 430/270.1 |
| 4,836,671 A | * | 6/1989 | Bautista | 356/3.1 |
| 4,915,112 A | | 4/1990 | Singer | |
| 4,970,137 A | | 11/1990 | Lewis et al. | |
| 5,002,852 A | | 3/1991 | Lewis et al. | |
| 5,170,549 A | | 12/1992 | Julien et al. | |
| 5,216,700 A | | 6/1993 | Cherian | |
| 5,420,000 A | | 5/1995 | Patel et al. | |
| 5,444,754 A | | 8/1995 | Wederhorn et al. | |
| 5,561,698 A | | 10/1996 | Mick et al. | |
| 5,623,139 A | | 4/1997 | Sliski | |
| 5,637,876 A | * | 6/1997 | Donahue et al. | 250/474.1 |
| 5,672,465 A | | 9/1997 | Patel et al. | |

(Continued)

FOREIGN PATENT DOCUMENTS

WO    2004/097709    11/2004

OTHER PUBLICATIONS

International Search Report of the International Searching Authority regarding International Application No. PCT/US06/23746 (Mar. 3, 2008).

(Continued)

*Primary Examiner*—Allen C. Ho
(74) *Attorney, Agent, or Firm*—William J. Davis

(57) ABSTRACT

An article of manufacture comprising a radiation sensitive material, and a measuring scale that is part of the radiation sensitive material. A method of measuring at least one parameter relating to an irradiated material is also described. A radiation sensitive material including a measuring scale is exposed to radiation and at least one parameter relating to one or more exposed areas of the material is measured by reference to the measuring scale on the material.

36 Claims, 1 Drawing Sheet

U.S. PATENT DOCUMENTS

| | | | |
|---|---|---|---|
| 6,014,470 A | 1/2000 | Matsuda | |
| 6,084,941 A | 7/2000 | Stenstrom | |
| 6,232,610 B1 | 5/2001 | Pageau et al. | |
| 6,333,970 B1 * | 12/2001 | LeMaitre et al. | 378/162 |
| 6,356,621 B1 * | 3/2002 | Furumori et al. | 378/162 |
| 6,364,529 B1 * | 4/2002 | Dawson | 378/207 |
| 6,646,273 B2 | 11/2003 | Ferralli | |
| 6,822,931 B2 | 11/2004 | Braunberger | |
| 6,927,859 B2 | 8/2005 | Kwok et al. | |
| 7,227,158 B1 * | 6/2007 | Patel et al. | 250/484.5 |
| 2001/0033682 A1 | 10/2001 | Robar et al. | |
| 2002/0048394 A1 | 4/2002 | Nagata et al. | |
| 2003/0095695 A1 | 5/2003 | Arnold | |
| 2003/0128276 A1 | 7/2003 | Boyd | |
| 2003/0129080 A1 | 7/2003 | Lewis et al. | |
| 2003/0129759 A1 | 7/2003 | Lewis et al. | |
| 2004/0086082 A1 | 5/2004 | Foos et al. | |
| 2004/0120560 A1 | 6/2004 | Robar et al. | |
| 2004/0197684 A1 | 10/2004 | Anyumba et al. | |
| 2004/0197700 A1 | 10/2004 | Anyumba et al. | |
| 2004/0211917 A1 | 10/2004 | Adamovics | |
| 2006/0145091 A1 * | 7/2006 | Patel | 250/474.1 |

OTHER PUBLICATIONS

Written Opinion of the International Searching Authority regarding International Application No. PCT/US06/23746 (Mar. 3, 2008).

Niroomand-Rad, A. et al., "Radiochromic Film Dosimetry," *Medical Physics*, vol. 25, Issue 11, pp. 2093-2115 (Nov. 1998).

Agazaryan, N. et al., "A methodology for verification of radiotherapy dose calculation," *J. Neurosurg.*, vol. 101, pp. 356-361 (Nov. 2004).

imPACT Information Leaflet 1: CT Scanner Acceptance Testing, Version 1.02 (May 18, 2001).

Butson, M.J. et al., "Visible absorption properties of radiation exposed XR type-T radiochromic film," *Physics in Medicine and Biology*, 49, N347-N351 (2004).

* cited by examiner

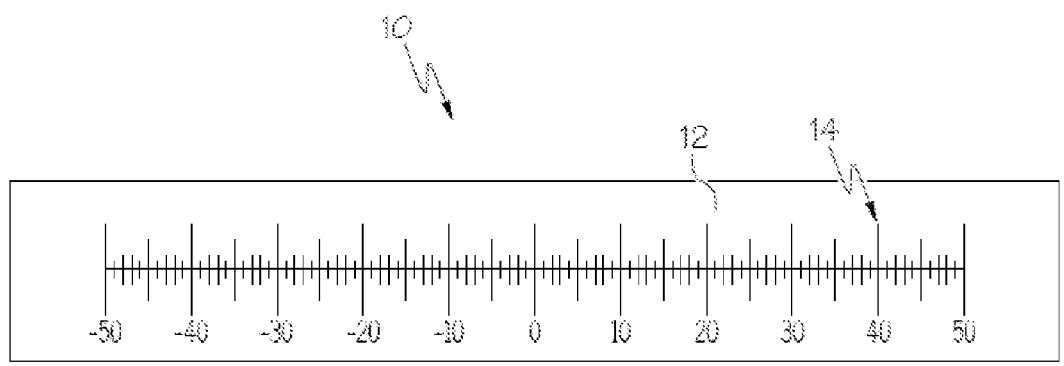

RADIATION SENSITIVE FILM INCLUDING A MEASURING SCALE

CROSS REFERENCE TO RELATED PATENT APPLICATION

This application corresponds to U.S. Provisional Patent Application Ser. No. 60/701,850, filed on Jul. 22, 2005.

BACKGROUND

In many types of radiation exposure processes a film is used to record an image. It is often necessary to provide some indication of the location or size of the image that appears on the film. It has been a common practice to use a conventional ruler to measure distances directly on the film after exposure and development. Also, it is common practice to place a ruler, a measuring tape, or other measuring reference object with graduation marks that are opaque to x-rays against or on the body and then take an x-ray. The graduation marks show up as an image on the developed x-ray film.

X-rays are important in giving detailed information about the image that appears on the film after developing. However, it is important that the amount of radiation that a patient is subjected to and that the radiation is directed toward the correct part of the patient's body during an x-ray, a scan, or radiation treatment for cancer.

High dose-rate brachytherapy involves the temporary placement of a small, almost point-sized, radioisotope radiation source within a living body. This is done for the purpose of irradiating and killing cancer cells. The characteristics of the radiation source are chosen so that cells close to the source receive very high radiation doses, whereas the dose to tissue a few millimeters away is much lower, below the threshold for permanent damage. The radiation source is usually affixed to the end of a thin wire that runs within a catheter. For treatment, the catheter is inserted into the body, passing through the treatment site. Since placement of the source close to the cancer cells is of extreme importance, it is necessary to validate that the source will move accurately to a pre-determined position within the catheter. Prior to treatment, it is necessary to validate that the source can be positioned with the requisite accuracy. Typically, this is done by fixing a strip of radiation-sensitive film within a test fixture. The radiation source is passed along the test fixture and stopped at predetermined points. The source dwells at predetermined points for a significant time to locally expose the radiation-sensitive film. At the end of the test the film is retrieved and measurements are made with a scale to demonstrate that the source has stopped at the correct predetermined positions.

X-ray computed radiography is an important and widely-used modality in medical and security imaging. For purposes of quality assurance, it is important to routinely measure the slice thickness, i.e., the width of the x-ray beam used in the examination. In order not to expose a patient to unnecessarily high levels of radiation during a CT exam, it is especially important to establish that the slice width is within CT machine-operating tolerances. The conventional way of establishing slice width is to place a piece of silver halide film in the CT machine and expose the film to a number of slice widths. Thereafter, the film is developed and a ruler is used to measure the width of the exposed areas.

The disadvantage of silver halide film is that the user cannot directly observe the position of the latent image of a slice-width exposure before repositioning the film to make second, third and fourth exposures, etc. As a result, there is a substantial likelihood that one or more exposures will overlap and the test exposures have to be repeated. Alternatively, the user could expose a single slice on a piece of film. However, this is wasteful since the slice thickness is frequently between 5 mm and 20 mm wide while the film is 8"×10", or greater, in size.

A common way to calibrate the dose response of radiation sensitive film is to place the film between two solid blocks and position the film so that it is parallel to a beam of radiation. The radiation dose to the film decreases with distance from the surface of the blocks upon which the radiation is incident. This is due to attenuation of the radiation in proportion to depth. The doses at particular distances from the incident surface are usually determined by using a primary measurement device such as an ion chamber placed at known depths in the solid blocks. When the film is exposed, the position of the film relative to the incident surface is carefully noted. After exposure, optical absorbance measurements are made on the film. Knowing the positions of the optical density measurements relative to their depths below the incident surface it is possible to relate the optical density of the film to the radiation dose at that depth and so construct a depth-dose curve.

In determining the depth-dose curve, optical absorption measurements may be made with a densitometer. However, this is a very laborious procedure requiring dozens of individual measurements in order to construct a detailed and accurate depth-dose response curve. A more convenient way to obtain the optical absorption data is to measure the film with an optical scanner. However, while this simplifies the collection of the absorption data, it introduces a greater uncertainty in knowing the depth corresponding to that measurement point because the scanner introduces spatial distortions into the scanned image.

In obtaining a radiograph of a patient, it is important that the portion of the patient that is to be examined be positioned in the center of the x-ray field. As a means of doing this, a light field is established in the radiography or mammography unit coincident with the x-ray field. The light field is projected onto the patient and the patient is then positioned so that the sight of the radiographic examination is centered within the light field.

In using the light field as a means for positioning patients, it is important to establish from time-to-time that the light field and x-ray fields are coincident. This test is commonly performed by a medical physicist one or more times per year on each radiography unit. The conventional way to do such a test was to align one or more pieces of silver halide film in light-proof envelopes so that they span the edges of the light field on all four sides. The edge of the light field is marked by pricking the envelopes with a small pin, thereby exposing the film to light. The film is then exposed to the x-ray beam. Following this, the film is taken to a darkroom and processed. Two problems can frequently occur. Thus, the pin-pricks may be too large and the film becomes overexposed making it difficult to accurately locate the edge of the light field. Another problem can occur if the film moves within the light-proof envelope after the pin-pricks have been made. A further inconvenience is that the film must be taken to a darkroom for development. Yet another inconvenience is that a ruler must be used to measure the positions of the pin-pricks and the edges of the x-ray field and determine the alignment of the light field with the radiation field.

Accordingly, there is a need for a radiation sensitive material comprising a support and a radiation sensitive composition that further includes a measuring scale to address the foregoing issues with the prior art. More specifically, there is a need for a radiochromic, self-developing film media that includes a measuring scale.

SUMMARY OF THE INVENTION

In one aspect, the present invention provides radiation sensitive material comprising a support, a radiation sensitive composition on the support, and a measuring scale. The measuring scale may be integral with or disposed on the support and/or the radiation sensitive composition.

In another aspect, the present invention provides a method of verifying the position of radiation using a radiation sensitive material having a measuring scale comprising the steps of: providing a radiation sensitive material including a measuring scale; exposing the radiation sensitive material to radiation; and measuring at least one parameter relating to the target radiation's exposure with the measuring scale. In accordance with more particular aspects of the invention, the method may further comprise adjusting the target radiation if the comparison with the measuring scale indicates an adjustment is needed; and repositioning the radiation sensitive material so that the steps of exposing, observing; comparing, and adjusting are repeated as needed.

Other aspects of the present invention will become apparent from the following description, the accompanying drawings and the appended claims.

BRIEF DESCRIPTION OF THE DRAWING

The FIGURE is a plan view showing an example of a radiation-sensitive material including a measuring scale in accordance with one aspect of the present invention.

DETAILED DESCRIPTION OF THE INVENTION

The following detailed description is intended to be representative only and not limiting as to radiation sensitive films that include a measuring scale. Many variations can be devised by one skilled in this area of technology, which are included within the scope of the present invention. The following detailed discussion of the various alternative and preferred embodiments will illustrate the general principles of the invention.

For the discussion below, the following terms are defined as follows:

The term "radiation sensitive" as used herein generally means that the exposure to radiation will cause a change in the film or composition applied thereto. The change may be immediately visible or may require a development process.

The term "radiochromic film" as used herein generally refers to film that changes when exposed to ionizing radiation, but experiences insignificant change from exposure to visible light or other forms of non-ionizing radiation.

The term "ionizing radiation" as used herein generally refers to radiation with a level of energy that is high enough to cause atoms to lose electrons and become charged or ionized. Ionizing radiation may be in the form of a high energy particles, like an alpha or beta particles, or in the form of electromagnetic waves, like gamma rays or x-rays. High energy particles and electromagnetic waves are released from the nuclei of radioactive atoms that are decaying or may be created by causing accelerated electrons to strike a metal target.

The term "low energy photon radiation" refers to photon radiation having an energy whereby at least 10% of energy transfer to an attenuator occurs through photoelectric absorption—see H. E. Johns and J. R. Cunningham in the $4^{th}$ Ed. (1983) of "The Physics of Radiology", p 140 et seq. Charles P. Thomas publisher.

The term "linear" in reference to a measuring scale as used herein generally means that the points or marks on the scale are separated by equal intervals. Thus, for example, the distance between mark ten (10) and mark twenty (20) is the same as the distance between mark ninety (90) and mark one hundred (100).

One embodiment of the present invention as illustrated in the FIGURE provides a radiation-sensitive material 10 comprising a radiation-sensitive composition 12 and a measuring scale 14. The radiation sensitive material may be radiographic or radiochromic film. In accordance with particular embodiments, a radiochromic film is used. GAFCHROMIC® radiochromic films manufactured by International Specialty Products are particularly useful. Specific examples of radiochromic films suitable for use in the present invention include, but are not limited to, those disclosed in U.S. Patent Application Publication 2003/0129759 to Lewis et al., published Jul. 10, 2003, which is incorporated herein in its entirety.

Although the present invention is not limited to a particular type of radiation-sensitive material, the following description relates to an embodiment of the invention based on the use of a particularly useful type of film. GAFCHROMIC® radiochromic film is self developing, not significantly sensitive to normal room light, and can be cut to a desired size. Exposure to ionizing radiation causes the radiochromic film to immediately change color, typically becoming darker. The degree of darkening is proportional to exposure and can be quantitatively measured with a densitometer or scanner.

The active component in the GAFCHROMIC® film media is a micro-particulate, radiation sensitive monomer that is dispersed in a gelatin matrix and coated onto a polyester film base. When the active monomeric component is exposed to ionizing radiation, a polymerization reaction is initiated, resulting in the production of a dye polymer. Since the polymer is by nature, a dye, the exposure produces coloration within the film. The active ingredient in accordance with particular embodiments comprises a long chain fatty acid belonging to a class of molecules known as diacetylenes. Many members of the diacetylene family are characteristically radiation sensitive only when there is intermolecular order, as, for instance, in a crystalline or micellar state. Suitable acetylenic compounds have the structure $A\text{-}(CH_2)_n\text{—}C\!\!=\!\!C\text{—}C\!\!=\!\!C\text{—}(CH_2)_m\text{-}B$, where n and m are both independently an integer of from about 0 to 20, more particularly from about 6 to 14, and A and B are independently a methyl group, a carboxyl group or metal carboxylate group. When exposed to radiation, active diacetylenes undergo a solid-state polymerization reaction producing a dye polymer referred to as a polydiacetylene. The color and spectral absorbance of polydiacetylene is specific to the particular molecular structure, but preferably the color change is clearly visible on the radiation sensitive film. The color change is frequently cyan blue, purple or magenta.

Specific examples of such polyacetylenes include, but are not limited to, pentacosa-10,12-diynoic acid; 13,15-octacosadiyne and docosa-10,12-diyne-1,22-dioic acid. Of these, pentacosa-10,12-diynoic acid is particularly useful since it provides unusually high sensitivity to ionizing radiation exposure. It is to be understood however, that dispersions of other normally crystalline, color developing polyacetylenes having a conjugated structure can be employed alone or in admixture with the preferred diynes as the image receptive layers of the present invention. Such compounds include the diynes of the above structure wherein the A and/or B moieties, in addition to lower alkyl or carboxyl, can also be hydroxy, amido, lower alkyl substituted amido, an aliphatic or aromatic carboxylate ester group having up to 10 carbon atoms, a mono- or di-valent carboxylate metal salt group, halo, carbamyl, lower alkyl substituted carbamyl or tosyl, as well as the corresponding triyne and tetrayne products of the above polyacetylenes having from about 20 to 60 carbon atoms and a conjugated structure. Examples of these compounds include 10,12-docosadiynediol, the ditoluene-p-sulfonate of 9,11-eicosadiynoic acid, the monoethyl ester of 10,12-docosadiynedioic acid, the lithium, sodium or potassium salt of 10,12-pentacosadiynoic acid, the zinc salt of heneicosa-10,12-diynoic acid, the manganese salt of eicosa-5,7-diynoic acid, 10,12-docosadiyne chloride, 10,12-pentacosadiyne (m-tolyl-urethane), 10,12-pentacosadiyne{[(butoxyl-carbonyl)-methyl]urethane}, N-(dimethyl)-10,12-pentacosadiynamide, N,N'-bis(a 1-methylbenzy-1) 10,12-pentacosadiyndiamide and the like. In addition, the diacetylenes for use in accordance with the invention generally may also have the formula:

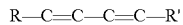

wherein R and R' are, for example, both $CH_2$—O—CON—H—$(CH_2)_5CH_3$. Such diacetylenes polymerize in the solid state either upon thermal annealing or exposure to high energy radiation. Suitable compounds are described in U.S. Pat. Nos. 5,420,000, 4,970,137, and 4,734,355, the contents of each of which are incorporated herein by reference. Preferably, the polyacetylenic compound has at least two conjugated acetylenic linkages and contains from about 10 to 60 carbon atoms.

Suitable compounds, which selectively absorb incident low energy photon radiation, are the metal halides and combinations thereof of Group I of the Periodic Table. These compounds may be added in an amount effective to selectively absorb the incident low energy photon radiation, and generally in an amount of from about 0.1% to 50.0%, and more particularly from about 2.5% to 20% by weight of the dispersion of the coating as described hereinafter.

In accordance with some aspects of the invention, such halides are selected from the group consisting of cesium and rubidium halides and in particular, cesium chloride, cesium bromide, cesium iodide and combinations thereof.

In addition, it is possible to add an additional compound, which may be a metal ion chelating agent or sequestering agent. The chelating agent can be added in amounts of from about 0.01% to 10.0%, and more particularly from about 0.1% to 2% by weight, based on the weight of the diacetylene compound. Typical chelating agents include disodium ethylenediaminetetraacetate, sodium oxalate, citric acid, sodium citrate, sodium tartrate, sodium polyphosphate, potassium hypophosphate, sodium diethyldithiocarbamate, the sodium salt of N,N,N',N'-ethylenediaminetetra(methylenephosphonic acid), the sodium salt of 1-hydroxyethane-1,1-diphosphonic acid and combinations thereof.

An opacifying agent may also be added to the radiochromic composition. Usually such an agent is a water insoluble metal compound wherein the metal component has an atomic number greater than 18. Examples of suitable compounds include oxides, carbonates, sulfates, sulfites, sulfides, carboxylates, phosphates, phosphates and silicates. An antioxidizing agent may also be added to the composition, usually in an amount of from about 0.01% to 5%, and more particularly from about 0.1 to 1% by weight of the weight of the diacetylene component. Suitable antioxidizing agents include propyl gallate, Tenoxo 6 (Tenox® is a trademark of the Eastman Chemical Company), Tenox® 2, Tenox® 7, Tenox® 20, sodium diethyldithiocarbamate, citric acid, sodium citrate, ascorbic acid, alkali metal sulfides and sulfites, 3-tert-butyl-4-hydroxy-5-methyl-phenyl sulfide, butylated hydroxytoluene, butylated hydroxyanisole, tert-butylhydroquinone, hydroxylamine and hydroxylamine hydrochloride.

The acetylenic component may also be sandwiched between two films in which one or both of the films may have the capability to filter or absorb light in the UV and/or visible wavelength regions. At least one of the films should be transparent in at least part of the visible spectrum.

In accordance with a particular method for preparing a radiochromic film useful herein, the polyacetylenic compound is dispersed in a non-solvating liquid and may be ripened or aged to maximize its radiation sensitivity. This dispersion may also contain a dissolved polymeric binder. Examples of binders include, but are not limited to, gelatin, agar, xanthan gum and polymers and copolymers containing maleic acid or acrylic acid residues, or salts thereof. The liquid dispersion is then applied onto the surface of a film, e.g., a polyester or similar film, and the coating is then dried. In particular, the normally crystalline or molecularly ordered polyacetylenic compound is dispersed into the non-solvating liquid in a concentration of from about 2 to 50% based on the combined weights of the polyacetylenic compound, the non-solvating liquid and the polymeric binder dissolved therein. The dispersion may then be aged or ripened by either (a) storing the composition at a temperature of from about 0 degrees C. to about 12 deg. C. for a period of from about 1 to 30 days, or (b) freezing the dispersion at a temperature between about −78 deg. C. and about −1 deg. C. for a period of time from about 1 to about 75 hours, or (c) heating the dispersion to a temperature between about 40 deg. C. and about 100 deg. C. for a period of time between about 10 minutes and 24 hours, or (d) a combination of any of the above techniques. This aging or ripening step is to be completed before drying the dispersion on the substrate.

In accordance with one aspect of the present invention, after the aging or ripening of the dispersion, a compound which selectively absorbs incident low energy photon radiation is mixed therewith in an amount which is effective to absorb incident low energy photon radiation when the dried composition is exposed thereto.

The thus mixed composition is then applied as a layer onto a substrate or support layer. Examples of substrates or supports that may be used include, but are not limited to, polymeric, metallic, glass, silicon and gallium arsenide. In accordance with a particular embodiment of the invention, the substrate or support layer may be a polymeric film which is permeable to low energy x-rays. The thus coated substrate is then dried at a temperature from about ambient up to about 100 deg. C. but below the distortion temperature of the substrate and below the decomposition temperature of any of the components of the coating or the melting point of the polyacetylene compound therein. The drying operation is generally conducted over a period of from about 20 seconds to about 10 hours and is typically effected at 15 deg. to 60 deg. C. for a period of from about 1 minute to about 5 hours.

The film thus formed is sensitive to radiation and, upon irradiation, a polymerization process is initiated in the polyacetylenic compound resulting in an immediate change in the color of the coating. The color darkens in proportion to the radiation exposure. The degree of darkening may be measured with a number of instruments including densitometers, spectrophotometers and film scanners. Generally when making such measurements, the color change of a transparent film sample would be assessed by measuring the proportion of light transmitted through the sample. Similarly, film coated on an opaque film base would be appropriately examined by measuring the proportion of light reflected from the sample.

Since the film darkens in proportion to radiation exposure, it is possible to measure the darkening and use this measurement as a means for determining the amount of the radiation exposure. Thus, the film may be employed as a radiation dosimeter, to measure and map radiation fields. Alternatively, the film may be used to record visual images such as those produced by radiographs, or autoradiographs.

The measuring scale included on or incorporated in the film may be linear, non-linear, or exponential. The scale may be in the form of a grid, pattern, or any shape suitable for measuring a parameter relating to an imaged film. For example, linear scales with divisions of 1 mm to several millimeters, circular or grid scales may be used. In accordance with certain embodiments, the measuring scale comprises a linear scale. The linear scale may include a series of lines made at equal intervals along one side of the radiochromic film. The scale may be in English units or metric units. In accordance with certain embodiments, the linear scale in metric, and more preferably is marked in millimeter intervals. Two or more measuring scales of the same or different types may be used in combination.

The lines that mark the intervals may be provided in accordance with various methods typically used for such purposes. By way of example, the lines or other marks may be printed, etched, embossed, marked, or cut onto the radiation sensitive film. The interval marks may be printed onto the film by hand using an ink pen or marker, by an ink-jet printer, by a laser-jet printer, by an ink stamp, by a foil stamp, by a transfer process, or by a machine printing press. The ink may contain a conventional colored, black or white pigment or the ink may be formulated with a component that is a strong attenuator of low energy photons. The scale may be cut into the radiation sensitive film by any of a variety of methods such as die-cut, a laser-cut, or a machine punch.

Another embodiment of the present invention relates to a method of verifying the position of radiation using the radiation sensitive film that includes a measuring scale. The method includes providing a radiation sensitive film, exposing the film to radiation and measuring at least one parameter relating to the radiation exposure by reference to the measuring scale included on the radiation sensitive film. The radiation may then be adjusted if the measurement taken from the radiation sensitive film indicates that an adjustment is necessary. Lastly, the radiation sensitive film may be repositioned within the pathway of the radiation so the above steps can be repeated until all measurements meet the specification of the particular machine, procedure, or patient.

The radiation may be any type of ionizing radiation. Preferably the ionizing radiation takes the form of alpha particles, beta particles, x-rays, Gamma rays, short wavelength UV, neutrons or charged particle radiation. These particles or rays may be formed by decaying radioactive atoms, or by accelerated electrons or other charged particles striking a metal target or causing a discharge in a volume of gas. In one embodiment of the present invention the radiation is gamma radiation produced by iridium, preferably iridium-192. In another embodiment of the present invention the radiation is x-ray radiation. X-rays are produced when electrons collide with the atoms and nuclei of a metal target.

The measuring scale included on the radiation sensitive film may be used to measure the radiation's amount of exposure, location, relative location, or movement. The measurement may be a specific number of millimeters along the edge of the radiation sensitive film to identify the location of the exposure. The measurement may be a comparison of the location of the radiation's exposure to another prior spot of exposure or to another field, like the field of visible light in conventional radiography. Also, the measurement may be a specific distance between successive exposures along the same piece of radiation sensitive film.

It would be possible to print on any radiographic and radiochromic films used to measure or record exposure to radiation. However, conventional radiographic films present at least three substantial difficulties that are not applicable to the printing of radiochromic film. Firstly radiographic films are light sensitive. This would make it difficult to proof, inspect or validate a printed scale. Secondly, radiographic films may be extremely sensitive to small levels of contaminants that could desensitize the active layer or cause objectionable levels of fog. Thirdly, radiographic films are chemically processed to develop the image. The chemical solutions are caustic and may react adversely with the printing inks.

The radiation sensitive film including a measuring scale can be used to validate the positioning of a radiation source. Radioisotope radiation can be placed within a patient's body to irradiate and kill cancer cells. The radiation source is moved quickly through the patient's body to the treatment site. The radiation sensitive film including a measuring scale is placed within a test fixture, so that the film will be exposed to the radiation. In the test fixture, the source is slowly moved through the fixture and stopped at predetermined points for sufficient time to expose the film. The pattern of radiation exposure on the film can be measured and compared to the scale as a means for directly measuring and validating the predetermined movement of the radiation source. Unlike conventional techniques, an external measurement device is not required.

The radiation typically used in this treatment is ionizing radiation. In accordance with a particular embodiment, an iridium-192 source is moved relative to the radiation sensitive film and is exposed to the gamma radiation that the iridium-192 emits. Since the preferred radiochromic film is self-developing, a pattern of radiation exposure develops on the film corresponding to locations where the movement of the iridium-192 source is paused. The measuring scale on the film may be used to observe and measure the distance between adjacent exposure spots, which resulted when the iridium-192 source is moved and paused repeatedly within the test device.

The radiation sensitive material including a measuring scale may be used to accurately determine the appropriate locations for taking optical absorption measurements. The absorption and the location measurement are used to construct a detailed and accurate depth-dose response curve. The radiation sensitive material, in this case a film, including a measuring scale is placed between two solid blocks with the film parallel to the target radiation. The radiation sensitive film is then exposed to the target radiation. The exposure is observed visually to measure and record a location for changes in density that occur on the radiation sensitive film. Each exposure can also be observed and measured using an optical scanner, which will measure and record the optical absorbance for each exposure. Furthermore, the presence of the scale ensures that measurements can properly be correlated with the correct locations on the film. Since the measuring scale is present on the radiation sensitive film prior to exposure, the scale can be registered with respect to the incident surface of the solid blocks. Accurate registration provides the operator with an accurate indication of where optical absorption measurements are being made, regardless of any image distribution introduced by the scanner.

A radiation sensitive film including a measuring scale may be used to directly measure the irradiated slice width of the x-ray beam in a CT machine (computed tomography machine). The target radiation in a CT machine is x-ray radiation. In accordance with this aspect of the invention, radiochromic film including a measuring scale is placed into a CT machine so that the film is in the pathway of the x-ray radiation. The CT machine is adjusted to set the slice width at a known value. Typically, the slice width may be set to provide nominal widths of between five millimeters to twenty millimeters. Usually, several different slice widths are measured. Any number of nominal slice width values may be exposed and measured.

Once a slice width is set to a chosen value, the radiation sensitive film is exposed to the target radiation. Exposure to radiation directly images the radiochromic film in an area corresponding to the slice width. Therefore, the slice width may be observed immediately by the CT machine operator. The slice width may be measured using the measuring scale on the film without moving the film. If the slice width and the measured exposure match within allowable tolerances, then the film can be adjusted so that a second slice width of greater or lesser value can be measured. If the slice width and the measured exposure do not match within allowable tolerances, then the film and the target radiation may both be adjusted and the same slice width may be exposed again. The film is adjusted between slice width trials so that the exposures that appear on the radiation sensitive film are each separate and distinct. The self-developing image obtained with a radiochromic film facilitates positioning of the film to expose a subsequent slice width without overlapping a previous exposure. After the film or target radiation or both are adjusted the steps may be repeated as many times as necessary.

A radiochromic film that includes a measuring scale may also be used to measure the coincidence between an x-ray field and the light field in a conventional radiographic unit. The light field is used to center the patient in the radiographic unit. Since the radiochromic film is not sensitive to light, all steps of the procedure can be performed in normal light. The film including a measuring scale is placed into a conventional radiographic unit such that the film spans the entire light field. The edge of the light field is aligned up with a special mark on the film's measuring scale that was previously designated as the zero mark or a zero mark may be made on the measuring scale with an ink pen or marker at the edge of the light field. Once the edge of the light field is aligned with the zero mark, the radiochromic film is exposed to the target radiation. The x-ray field will be observable on the film as a darkened area. If the x-ray field and the light field are aligned properly, then the darkened area will stop at the zero mark. If the darkened area is beyond the zero mark or falls short of the zero mark, then the distance between the edge of the darkened area and the zero mark can be quickly read using the measuring scale on the radiation sensitive film. The difference can be read immediately without moving or picking up the film. Any difference in the x-ray field and the light field may be corrected by adjusting the conventional radiographic unit. Then, another trial can be run after repositioning the film or placing a new piece of film into the conventional radiographic unit.

For conventional radiographic units that have an electronic image receptor that shows the x-ray image on a monitor, the measuring scale on the radiation sensitive film may measure whether the x-ray field is correctly aligned with the image receptor. In accordance with this embodiment of the invention, the measuring scale may be printed, etched, embossed, punched, die-cut, laser-cut, or marked on the film substrate so that the scale will appear on the monitor along with the x-ray image. In accordance with particular aspects of the invention, the scale may be either more opaque or less opaque to x-rays than the film substrate. The radiation sensitive film including a measuring scale is placed in the conventional radiographic unit so that the film is in the pathway of the x-rays. The position of the edges of the x-ray image on the monitor screen are recorded with respect to the measuring scale from the radiation sensitive film that is now visible on the monitor screen. Then, the darkened area of exposure on the radiation sensitive film is observed and its edges are measured and recorded with respect to the measuring scale. The measurements of the x-ray images edges and the edges of the darkened area of exposure should be the same if the x-ray field is correctly aligned with the image receptor. If the measurements are not the same, then the conventional radiographic unit or the image receptor needs adjusted. The radiation sensitive film may be repositioned or a new piece may be placed in the conventional radiography unit so the steps may be repeated until the x-ray field and the image receptor are aligned.

A radiochromic film that includes a measuring scale comprising a printed grid may also be used to measure and correct spatial distortions produced when an image is digitized in a film scanner. The ink used to print the grid pattern may be black, white, colored or transparent in the visible spectrum. In one particular embodiment the color or optical absorption of the ink may be chosen so that the ink absorbs light over a selected range of wavelengths, but transmits light over a different range of wavelengths. This embodiment would be particularly useful when the radiochromic film image is digitized with a color film scanner. GAFCHROMIC EBT film, for instance, is used to validate doses in intensity modulated radiation therapy (IMRT). In IMRT treatment plan validation it is essential to provide an accurate spatial representation of the radiation doses in two dimensions. Thus errors in measuring a dose level as well as errors caused by spatial distortions of a scanned image will combine to create differences between the measurements and the treatment plan. In this application the color changes in the diacetylenic active layer are related to radiation dose. In a first step the film response is calibrated by exposing the radiochromic film to a set of known radiation doses. The film response is then measured in the red color channel of an rgb film scanner. Subsequently an IMRT treatment plan is exposed on one or more additional pieces of the radiochromic film. These films are then scanned in the red color channel of the same scanner and the calibration data is used to create a two-dimensional map of the measured doses that are subsequently compared with the treatment plan. If the radiochromic film is printed with a two-dimensional grid an image of the grid could be used to rectify distortions caused by the scanner. However, it will be apparent that the grid will interfere with dose measurement if the printing ink absorbs light in the red color channel of the scanner. In contrast, if the printing ink is transparent in the red color channel, but absorbs light in either or both of the blue or green color channels, then the printing will not interfere with the dose measurement. However, the grid will be observable in the image provided by at least one of the other color channels and hence provides a means of rectifying spatial distortions without interfering with dose measurement. The dimensions of the grid in the image should be adjusted to correspond to the dimension of the original grid. One of ordinary skill in the art is capable of selecting the appropriate technique for correcting the image. Examples of methods for correcting distortion in an image are described in U.S. Pat.

No. 6,014,470 and U.S. Patent Application Publication Nos. 2002/0048394 and 2003/0128276, the contents of which are hereby incorporated by reference.

Therefore, in accordance with particular embodiments of the invention, the radiation-sensitive material is a radiochromic film that absorbs visible light over a first portion of the visible spectrum. The scale or grid, by contrast, may be effectively transparent over the first portion of the visible spectrum and absorb light over a second portion of the visible spectrum. The term "effectively transparent" as used herein indicates that the amount of absorbance over a selected portion of the spectrum is low enough that it does not interfere with the measurement of absorbance of the imaged radiochromic film over the selected portion of the spectrum.

The following, non-limiting examples illustrates particular aspects of the present invention.

EXAMPLE 1

A linear scale was printed onto GAFCHROMIC RTQA film in a HP Laser-Jet printer. The divisions on the printed scale were exactly 1 mm. During the printing cycle in the Laser-Jet printer, the film is heated to fuse the toner particles to the film. Such heating could potentially desensitize, or otherwise diminish the quality of the film. When the printed film was exposed to a 50 cGy dose of x-rays (150 kVp, 1 mm A1 filtration) it was evident that the properties of the film had not been harmed.

EXAMPLE 2

A sample of the film from Example 1 was placed in a holder and an Ir192 radiation source was stepped along the film, dwelling for about 1 second at 5 mm intervals during the travel. The time to transit between adjacent points was much less than 1 second. When the film was examined, a series of darkened spots was evident. The spots were consistently spaced at 5 mm intervals verifying that the source had moved in 5 mm increments.

EXAMPLE 3

Using an HP Laser-Jet printer a linear metric scale with mm rulings was printed on a piece of radiochromic film approximately 25 cm in length. The film was placed in an x-ray CT machine and an exposure with 5 mm slice width was made. The film was repositioned and a 10 mm slice was exposed. Again the film was repositioned and a 20 mm slice was exposed. The exposed areas did not overlap because it was easy to position the film between exposures. The width of the exposed slices was easily and directly determined by reference to the printed scale.

EXAMPLE 4

Using a Quick Label QLS-500 thermal transfer printer a linear metric scale with mm rulings was printed repeatedly on a 5" wide roll of radiochromic film. The scale was 10 cm long and oriented perpendicular to the length of the roll. The scales were printed 0.75" apart. After printing the roll was cut into 0.75"×5" strips each containing one of the printed metric scales. A printed film strip was then placed in an x-ray CT machine and an exposure with 5 mm slice width was made. The film was repositioned and a 10 mm slice was exposed. Again the film was repositioned and a 20 mm slice was exposed. The exposed areas did not overlap because it was easy to position the film between exposures. The width of the exposed slices was easily and directly determined by reference to the printed scale.

Although the present invention is shown and described with respect to certain aspects, it is obvious that various modifications will become apparent to those skilled in the art upon reading and understanding the specification and the appended claims. The present invention includes all such improvements and modifications and is limited only by the scope of the claims.

What is claimed:

1. A radiation-sensitive material comprising a radiochromic self-developing film, wherein said radiochromic self-developing film comprises:
 a. a support layer;
 b. a radiation sensitive composition disposed on said support layer; and
 c. a measuring scale of known dimensions for measuring a dimension or a location on the radiation-sensitive material;
 wherein said measuring scale is integral with or disposed on said radiation sensitive material and said radiochromic self-developing film forms an image in response to radiation exposure, said image absorbing visible light over a first portion of the visible spectrum and said scale absorbing visible light over a second portion of the visible spectrum such that the scale is effectively transparent over the first portion of the visible spectrum.

2. The radiation-sensitive material of claim 1, wherein said radiochromic self-developing film includes a substantially crystalline image receptive polyacetylenic compound having the structure:

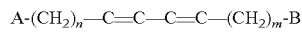

$$A\text{-}(CH_2)_n\text{---}C\!\!=\!\!C\text{---}C\!\!=\!\!C\text{---}(CH_2)_m\text{-}B$$

wherein m and n are both independently an integer from 6 to 14 and A and B are independent from one another and are selected from the group consisting of methyl, carboxyl, hydroxy, amido, lower aklyl substituted amido, aliphatic or aromatic carboxylate ester group having up to 10 carbon atoms, mono- or di-valent carboxylate metal salt group, halo, carbamyl, lower aklyl substituted carbamyl or tosyl, triyn or tetrayne products of the above polyacetylenes having from 20 to 60 carbon atoms and a conjugated structure, and combinations thereof.

3. The radiation-sensitive material of claim 1, wherein said radiation-sensitive material comprises a radiation-sensitive film and said measuring scale is printed onto said radiation sensitive film.

4. The radiation-sensitive material of claim 3, wherein said measuring scale is printed onto said radiation sensitive film with conventional pigment ink.

5. The radiation-sensitive material of claim 1, wherein said measuring scale is more opaque to x-rays than the support layer or less opaque to x-rays than the support layer.

6. The radiation-sensitive material of claim 1, wherein said measuring scale is cut into the radiation sensitive material.

7. The radiation-sensitive material of claim 6, wherein the measuring scale is die cut or laser cut into the radiation-sensitive material.

8. The radiation-sensitive material of claim 1, wherein said measuring scale is embossed onto said radiation sensitive material.

9. The radiation-sensitive material of claim 1, wherein said measuring scale is etched onto said radiation sensitive material.

10. The radiation-sensitive material of claim 1, wherein said measuring scale is linear.

11. The radiation-sensitive material of claim 10, wherein said measuring scale is a metric scale.

12. The radiation-sensitive material of claim 11, wherein said linear scale comprises a plurality of graduation marks spaced at one millimeter increments.

13. The radiation-sensitive material of claim 1, wherein said measuring scale comprises a two-dimensional scale or grid.

14. A method of measuring dimension or location on an irradiated material comprising the steps of:
 a. exposing a radiation-sensitive material comprising a measuring scale to radiation to form an exposed material; and
 b. measuring at least one of a dimension or a location relating to one or more exposed areas of the material by reference to the measuring scale on the radiation sensitive material, wherein said radiation-sensitive material comprises a radiochromic self-developing film that forms an image in response to radiation exposure, said image absorbing visible light over a first portion of the visible spectrum and said scale absorbing visible light over a second portion of the visible spectrum such that the scale is effectively transparent over the first portion of the visible spectrum.

15. The method of claim 14, wherein the at least one of a dimension or a location relates to the size of an exposed area or the location of an exposed area on the material.

16. The method of claim 14, wherein said radiochromic self-developing film includes a substantially crystalline image receptive polyacetylenic compound having the structure:

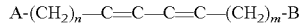

$$A\text{-}(CH_2)_n\text{---}C{\equiv}C\text{---}C{\equiv}C\text{---}(CH_2)_m\text{-}B$$

wherein m and n are both independently an integer from 6 to 14 and A and B are independent from one another and are selected from the group consisting of methyl, carboxyl, hydroxy, amido, lower aklyl substituted amido, aliphatic or aromatic carboxylate ester group having up to 10 carbon atoms, mono- or di-valent carboxylate metal salt group, halo, carbamyl, lower aklyl substituted carbamyl or tosyl, triyne or tetrayne products of the above polyacetylenes having from 20 to 60 carbon atoms and a conjugated structure, and combinations thereof.

17. The method of claim 16, wherein the mono-valent carboxylate metal salt is a lithium salt.

18. The method of claim 16, wherein said step of exposing the material comprises placing said radiochromic self-developing film comprising a measuring scale between two solid blocks, positioning the film parallel to a beam of radiation and exposing the film to said beam of radiation.

19. The method of claim 18, further comprising scanning one or more of the exposed areas with an optical scanner.

20. The method of claim 19, wherein the optical scanner collects data in over more than one band of wavelengths.

21. The method of claim 20, wherein the optical scanner is an rbg color scanner.

22. The method of claim 19, wherein said at least one parameter comprises a distance from an incident surface to an exposed area.

23. The method of claim 22, further comprising the step of constructing a depth-dose curve.

24. The method of claim 14, wherein said step of exposing the material comprises exposing said film to a radioisotope radiation source.

25. The method of claim 24, wherein said radioisotope radiation source exposes a first location on said film and a second location a predetermined distance away from said first location and said at least one of a dimension or a location is the distance from said first location to said second location.

26. The method of claim 14, wherein said step of exposing said material comprises placing said radiochromic self-developing film comprising a measuring scale into a CT machine and exposing said film to an x-ray beam having a first slice width.

27. The method of claim 26, wherein said first slice width is set to a nominal value between about five millimeters and about twenty millimeters.

28. The method of claim 26, wherein said at least one of a dimension or a location comprises the width of the exposed area.

29. The method of claim 26, further comprising repositioning said radiochromic self-developing film and exposing to an x-ray beam having a second slice width.

30. The method of claim 14, wherein said step of exposing said material comprises positioning the radiochromic self-developing film in a radiographic unit comprising an x-ray field and a light field, aligning the film with the light field, and exposing said film to the x-ray field.

31. The method of claim 30, wherein said measuring scale on said radiochromic self-developing film spans the edge of said light field.

32. The method of claim 31, wherein said step of measuring comprises determining the distance between said edge of said light field and said x-ray field by reference to said measuring scale.

33. The method of claim 32, wherein said measuring scale is more opaque to x-rays or less opaque to x-rays relative to the remainder of the film.

34. The method of claim 14, further comprising capturing an image of said exposed material.

35. The method of claim 34, wherein the at least one of a dimension or a location comprises verifying alignment of an x-ray field with an image receptor used to capture said image.

36. A method for correcting distortion in a scanned image comprising:
 a. obtaining a scanned image of a radiation-sensitive material comprising a measuring scale of known dimensions; and
 b. rectifying distortion in the scanned image by adjusting the dimensions of the measuring scale in the scanned image to correspond to the known dimensions of the measuring scale in the radiation-sensitive material, wherein said radiation-sensitive material comprises a radiochromic self-developing film that forms an image in response to radiation exposure, said image absorbing visible light over a first portion of the visible spectrum and said scale absorbing visible light over a second portion of the visible spectrum such that the scale is effectively transparent over the first portion of the visible spectrum.

* * * * *